(12) United States Patent
Martucci et al.

(10) Patent No.: US 7,794,934 B2
(45) Date of Patent: Sep. 14, 2010

(54) PREDICTING NEGATIVE SYMPTOM CHANGE DURING DRUG TREATMENT

(75) Inventors: Livia Martucci, London (GB); James Kennedy, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 0 days.

(21) Appl. No.: 11/394,187

(22) Filed: Mar. 31, 2006

(65) Prior Publication Data

US 2007/0231801 A1 Oct. 4, 2007

(51) Int. Cl.
*C12Q 1/68* (2006.01)
*C07H 21/04* (2006.01)
*C12P 19/34* (2006.01)

(52) U.S. Cl. .......................... 435/6; 536/24.3; 435/91.2

(58) Field of Classification Search ........................ None
See application file for complete search history.

(56) References Cited

OTHER PUBLICATIONS

Williams et al (Molecular Psychiatry (2002) vol. 7, pp. 508-514).*
Gupta (Future Medicine (2006) vol. 7, pp. 31-47).*
Reynolds et al (Expert Opinions in Pharmacotherapy (2006) vol. 7, pp. 1429-1440).*
Race, Ethnicity, and Genetics Work Group (American Journal of Genetics (2005) vol. 77, pp. 519-532).*
Sankar et al (Science (2002) vol. 298, pp. 1337-1338).*
Martucci et al (Schizophrenia Research (2006) vol. 84, pp. 214-221).*
Hong et al (Psychiatric Genetics (2001) vol. 11, pp. 219-222).*
Chiu et al (Neuropyschobiology (2003) vol. 47, pp. 178-181).*
Lane et al ( J. Clin. Psychiatry (1999) vol. 60, pp. 36-40).*
Xie et al (Annuals Review of Pharmacology and Toxicology (2001) vol. 41, pp. 815-850).*
Hirschhorn et al. (Genetics in Medicine. vol. 4, No. 2, pp. 45-61, Mar. 2002).*
Gene card GRIN2B, GC12M013605 www.genecards.org/cgi-bin/carddisp.pl?gene=GRIN2B&search=grin2b&suff=txt, pp. 1-11), 2007.*
Martucci et al (Schizophrenia Bulletin (2005) vol. 31: 271-272).*
Tsai et al (Journal of Neural Transmission (2002) vol. 109, pp. 483-488).*
Angrist, B. et al., "Partial improvement in negative schizophrenic symptoms after amphetamine", Psychopharmacology vol. 78, No. 2, p. 128-130, (1982).
Arvanov, V. L. et al., "M100907, a selective 5-HT2A receptor antagonist and a potential antipsychotic drug, facilitates N-methyl-D-aspartate-receptor mediated neurotransmission in the rat medial prefrontal cortical neurons in vitro", Neuropsychopharmacology vol. 18, No. 3, p. 197-209, (1998).
Arvanov, V. L. et al., "Clozapine and haloperidol modulate N-methyl-D-aspartate- and non-N-methyl-D-aspartate receptor-mediated neurotransmission in rat prefrontal cortical neurons in vitro", The Journal of Pharmacolology and Experimental Therapeutics, vol. 283, No. 1, p. 226-234, (1997).

Basile, V.S. et al., "Pharmacogenomics in schizophrenia: the quest for individualized therapy", Human Molecular Genetics, vol. 11, No. 20, p. 2517-2530, (2002).
Beasley, C. M. et al., "Efficacy of olanzapine: an overview of pivotal clinical trials", J Clin Psychiatry vol. 58, Suppl.10, p. 7-12, (1997).
Bhana, N. et al., "Olanzapine: an updated review of its use in the management of schizophrenia", Drugs, vol. 61, No. 1, p. 111-161, (2001).
Carlsson, M. et al., "Schizophrenia: a subcortical neurotransmitter imbalance syndrome", Schizophrenia Bulletin, vol. 16, No. 3, p. 425-432, (1990).
Chen, L. et al, "Interaction of dopamine D1 and NMDA receptors mediates acute clozapine potentiation of glutamate EPSPs in rat prefrontal cortex", J Neurophysiol, vol. 87, No. 5, p. 2324-2336, (2002).
Chiu, H. J. et al, "Association analysis of the genetic variants of the N-methyl D-aspartate receptor subunit 2b (NR2b) and treatment-refractory schizophrenia in the Chinese", Neuropsychobiology, vol. 47, No. 4, p. 178-181, (2003).
Corbett, R. et al., "Antipsychotic agents antagonize non-competitive N-methyl-D-aspartate antagonist-induced behaviors", Psychopharmacology, vol. 120, No. 1, p. 67-74, (1995).
Costa, J. et al, "An open trial of glycine as an adjunct to neuroleptics in chronic treatment-refractory schizophrenics", J Clin Psychopharmacol, vol. 10, No. 1, p. 71-72, (1990).
Daly,D. A. et al, "Actions of clozapine and haloperidol on the extracellular levels of excitatory amino acids in the prefrontal cortex and striatum of conscious rats", Neuroscience Letters, vol. 152, No. 1&2, p. 61-64, (1993).
Davis, K. L. et al, "Dopamine in Schizophrenia: a review and reconceptualization", Am J Psychiatry, vol. 148, No. 11, p. 1474-1486, (1991).

(Continued)

*Primary Examiner*—Steven C Pohnert
(74) *Attorney, Agent, or Firm*—Westerman, Hattori, Daniels & Adrian, LLP

(57) ABSTRACT

A method for predicting a negative symptom change in a subject during drug therapy is provided. The method comprises isolating genomic DNA from a sample of the subject, and genotyping a T5988C marker of GRIN2B gene. A GRIN2B 5988 T/T genotype is predictive of a negative symptom improvement in the subject in response to drug therapy. The drug therapy may be clozapine therapy. Also provided is a method of identifying a polymorphism in a nucleotide sequence of interest that is predictive of response to drug therapy comprising the steps of assessing negative symptom improvement in a plurality of subjects during the course of drug therapy, isolating a sample comprising DNA from each subject, genotyping one or more nucleotide sequences of interest in the DNA of each subject to identify one or more polymorphisms that exist in the one or more nucleotide sequences of interest, wherein correlation of a significant improvement of negative symptoms with one or more polymorphisms is predictive of response to drug therapy.

12 Claims, No Drawings

OTHER PUBLICATIONS

Farber, N. B. et al., "Olanzapine and fluperlapine mimic clozapine in preventing MK-801 neurotoxicity", Schizophrenia Reasearch, vol. 21, No. 1, p. 33-37, (1996).

Farber, N. B. et al., "Antipsychotic drugs block phencyclidine receptor-mediated neurotoxicity", Biol Psychiatry, vol. 34, No. 1&2, p. 119-121, (1993).

Fletcher, E. J. et al., "Haloperidol interacts with the strychnine-insensitive glycine site at the NMDA receptor in cultured mouse hippocampal neurones", European Journal of Pharmacology, vol. 235, No. 2&3, p.291-295, (1993).

Goff, D. C. et al., "The emerging role of glutamate in the pathophysiology and treatment of schizophrenia", Am J Psychiatry, vol. 158, No. 9, p. 1367-1377, (2001).

Goff, D. C. et al., "D-cycloserine added to clozapine for patients with schizophrenia", Am J Psychiatry, vol. 153, No. 12, p. 1628-1630, (1996).

Goff, D. C. et al., "A placebo-controlled trial of D-cycloserine added to conventional neuroleptics in patients with schizophrenia", Arch Gen Psychiatry, vol. 56, No. 1, p. 21-27, (1999).

Hagger, C. et al., "Improvement in cognitive functions and psychiatric symptoms in treatment-refractory schizophrenic patients receiving clozapine", Biol Psychiatry, vol. 34, No. 10, p. 702-712, (1993).

Healy, D. J. et al., "Clozapine and haloperidol differentially affect AMPA and kainate receptor subunit mRNA levels in rat cortex and striatum", Molecular Brain Research, vol. 47, No. 1&2, p. 331-338, (1997).

Heresco-Levy, U. et al., "Double-blind, placebo-controlled, cross-over trial of glycine adjuvant therapy for treatment-resistant schizophrenia", British Journal of Psychiatry, vol. 169, No. 5, p. 610-617, (1996).

Hong, C. J. et al., "Association analysis for NMDA receptor subunit 2B (GRIN2B) genetic variants and psychopathology and clozapine response in schizophrenia", Psychiatric Genetics, vol. 11, No. 4, p. 219-222, (2001).

Jardemark, K. E. et al., "Biphasic modulation of NMDA-induced responses in pyramidal cells of the medial prefrontal cortex by Y-931, a potential atypical antipsychotic drug", Synapse, vol. 41, No. 4, p. 294-300, (2001).

Javitt, D. C., "Management of negative symptoms of schizophrenia", Current Psychiatry Reports, vol. 3, No. 5, p. 413-417, (2001).

Javitt, D. C. et al, "Amelioration of negative symptoms in schizophrenia by glycine", Am J Psychiatry, vol. 151, No. 8, p. 1234-1236, (1994).

Lidsky, T. I. et al, "Anti-glutamatergic effects of clozapine", Neuroscience Letters, vol. 163, No. 2, p. 155-158, (1993).

Lidsky, T.I. et al, "Antipsychotic drug effects on glutamatergic activity", Brain Research, vol. 764, No. 1&2, p. 46-52, (1997).

Malhotra, A. K. et al., "Pharmacogenetics of psychotropic drug response", vol. 161, No. 5, p. 780-796, (2004).

McCoy, L. et al., "Chronic antipsychotic treatment alters glycine-stimulated NMDA receptor binding in rat brain", Neuroscience Letters, vol. 213, No. 2, p. 137-141, (1996).

Meador-Woodruff, J. H. et al., "Glutamate receptor expression in schizophrenic brain", Brain Research Reviews, vol. 31, No. 2&3, p. 288-294, (2000).

Meador-Woodruff, J. H. et al., "Differential regulation of hippocampal AMPA and kainate receptor subunit expression by haloperidol and clozapine", Molecular Psychiatry, vol. 1, No. 1, p. 41-53, (1996).

Meshul, C. K., et al., "Haloperidol-induced morphological alterations are associated with changes in calcium/ calmodulin kinase II activity and glutamate immunoreactivity", Synapse, vol. 18, No. 3, p. 205-217, (1994).

Ninan, I. et al., "Modulation of the ability of clozapine to facilitate NMDA- and electrically evoked responses in pyramidal cells of the rat medial prefrontal cortex by dopamine: pharmacological evidence", European Journal of Neuroscience, vol. 17, No. 6, p. 1306-1312, (2003).

Nomikos, G. G. et al., "Systemic adminstration of amperozide, a new atypical antipsychotic drug, preferentially increase dopamine release in the rat medial prefrontal cortex", Psychopharmacology, vol. 115, No. 1&2, p. 147-156, (1994).

Olney, J. W. et al., "Efficacy of clozapine compared with other antipsychotics in preventing NMDA-antagonist neurotoxicity", J Clin Psychiatry, vol. 55, Suppl B, p. 43-46, (1994).

Olney, J. W. et al., "Glutamate receptor dysfunction and schizophrenia", Arch Gen Psychiatry, vol. 52, No. 12, p. 998-1007, (1995).

Riva, M. A., et al., "Regulation of NMDA receptor subunit messenger RNA levels in the rat brain following acute and chronic exposure to antipsychotic drugs", Molecular Brain Research, vol. 50, No. 1&2, p. 136-142, (1997).

Rosse, R. B., et al., "Glycine adjuvant therapy to conventional neuroleptic treatment in schizophrenia: an open-label, pilot study", Clinical Neuropharmacology, vol. 12, No. 5, p. 416-424, (1989).

Tollefson, G. D. et al., "Negative symptoms: a path analytic approach to a double-blind, placebo- and haloperidol-controlled clinical trial with olanzapine", Am J Psychiatry, vol. 154, No. 4, p. 466-474, (1997).

Van Kammen, D. P. et al., "Dextro-amphetamine diminished negative symptoms in schizophrenia", International Clinical Psychopharmacology, vol. 3, No. 2, p. 111-121, (1988).

Wang, J. et al., "D1 dopamine receptors potentiate NMDA-mediated excitability increase in layer V prefrontal cortical pyramidal neurons", Cerebral Cortex, vol. 11, No. 5, p. 452-462, (2001).

Wang, R. Y. et al., "M100907 and clozapine, but not haloperidol or raclopride, prevent phencyclidine-induced blockade of NMDA responses in pyramidal neurons of the rat medial prefrontal cortical slice", Neuropsychopharmacology, vol. 19, No. 1, p. 74-85, (1998).

Watanabe, M. et al., "The atypical antipsychotic sertindole enhances efflux of dopamine and its metabolites in the rat cortex and striatum", European Journal of Pharmacology, vol. 367, No. 1, p. 19-23, (1999).

Watson, G. B. et al., "D-cycloserine acts as a partial agonist at the glycine modulatory site of the NMDA receptor expressed in Xenopus oocytes", Brain Research, vol. 510, No. 1, p. 158-160, (1990).

Waziri, R., "Glycine therapy of schizophrenia", Biol Psychiatry, vol. 23, No. 2, p. 210-211, (1988).

Weinberger, D. R. et al., "Physiologic dysfunction of dorsolateral prefrontal cortex in schizophrenia I. Regional cerebral blood flow evidence", Arch Gen Psychiatry, vol. 43, No. 2, p. 114-124, (1986).

Weinberger, D. R. et al., "Physiological dysfunction of dorsolateral prefrontal cortex in schizophrenia III. A new cohort and evidence for a monoaminergic mechanism", Arch Gen Psychiatry, vol. 45, No. 7, p. 609-615, (1988).

Westerink, B. H., et al., "Antipsychotic drugs induce similar effects on the release of dopamine and noradrenaline in the medial prefrontal cortex of the rat brain", European Journal of Pharmacology, vol. 361, No. 1, p.27-33, (1998).

Yamamoto, B. K., et al., "Brain region effects of clozapine on amino acid and monoamine transmission", J Clin Psychiatry vol. 55, Suppl B, p. 8-14, (1994).

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
cttgagccca gagtgaacac t                                            21

<210> SEQ ID NO 2
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 2
accctcatcc ctggagtttt ataca                                        25
```

PREDICTING NEGATIVE SYMPTOM CHANGE DURING DRUG TREATMENT

The present invention relates to DNA polymorphisms. More specifically, the present invention relates to DNA polymorphisms that are predictive of a subject's response to drug treatment.

BACKGROUND OF THE INVENTION

Dopamine D2 receptor blockade is currently the main mechanism through which most antipsychotic medications (AP) are thought to work. However, both dopamine and glutamate in the prefrontal cortex appear to have an important role in the symptomatology of schizophrenia (Weinberger, Berman et al. 1986; Carlsson and Carlsson 1990; Wang and O'Donnell 2001).

Atypical antipsychotics appear to be more effective than classical antipsychotics in treating schizophrenia negative symptoms and cognitive dysfunction (Bhana, Foster et al. 2001; Javitt 2001). Interestingly, compared to classical AP, atypical AP preferentially increase glutamate (Daly and Moghaddam 1993; Yamamoto, Pehek et al. 1994) and dopamine release (Nomikos, Iurlo et al. 1994; Westerink, de Boer et al. 1998; Watanabe and Hagino 1999) in the medial prefrontal cortex.

By itself, the dopamine hypothesis cannot account for the observation that several weeks of antipsychotic treatment are required for what may be suboptimal clinical response, and why negative symptoms often do not improve with typical antipsychotics. Paradoxically, stimulant treatment can actually improve the negative symptoms of schizophrenia (Angrist, Peselow et al. 1982; van Kammen and Boronow 1988). The dopamine hypothesis has evolved into a theory of cortical-subcortical dopamine imbalance, with excess subcortical dopamine function associated with positive symptoms, and dopaminergic hypoactivity underlying negative symptoms (Weinberger, Berman et al. 1988; Davis, Kahn et al. 1991). Cortical and subcortical structures are functionally linked via the neurotransmitter glutamate, so disruption of glutamatergic neurotransmission could lead to the dissociation of dopaminergic function in these regions predicted by this model (Carlsson and Carlsson 1990). The involvement of glutamate in the pathophysiology of schizophrenia is further supported because there is pharmacological evidence that glutamatergic hypoactivity may itself be associated with the illness (Meador-Woodruff and Healy 2000).

The schizophrenia-like syndrome generated by antagonists such as phencyclidine (PCP) to the NMDA glutamate receptor resembles the disorder even more closely than that induced by dopamine agonists, as it includes negative symptoms as well as cognitive deficits. Pharmacological agents that act on glutamatergic receptors differentiate themselves from more traditional antidopaminergic agents in their ability to improve negative symptoms. Antipsychotic drugs in general can affect glutamatergic neurotransmission at clinically therapeutic concentrations by altering the presynaptic release of excitatory amino acid and also the density or subunit composition of glutamate receptors (Arvanov, Liang et al. 1997; Arvanov and Wang 1998; Chen and Yang 2002) The glutamatergic effects of antipsychotics are importantly concentration-dependent and, depending on their relative dose-response curves, different agents may act either as agonists or antagonists at therapeutic concentrations.

Growing evidence suggests that the effects of certain atypical antipsychotics on NMDA receptors may be a key differentiation of these agents from conventional antipsychotics. Corbett et al. (Corbett, Camacho et al. 1995) reported that olanzapine and clozapine, but not haloperidol or risperidone, reversed PCP-induced social withdrawal in rats. Olanzapine, clozapine, and fluperlapine strongly prevented the neurotoxicity induced by NMDA receptor antagonists, whereas haloperidol and thioridazine displayed intermediate effectiveness (Farber, Price et al. 1993; Olney 1994; Olney and Farber 1994; Farber, Foster et al. 1996). Both the selective 5-HT2A antagonist M100907 and clozapine prevented PCP-induced blockade of NMDA receptors (Wang and Liang 1998), whereas selective D2 blockers had no effect. Lidsky et al. (Lidsky, Yablonsky-Alter et al. 1993) found that clozapine, and not haloperidol displaced the ligand [3H]MK801 from the NMDA receptor at therapeutic levels. Arvanov et al. (Arvanov, Liang et al. 1997) found that clozapine but not haloperidol produced an enhancement of NMDA-receptor-mediated neurotransmission.

Consistent with these results, Ninan et al have demonstrated that atypical antipsychotic drugs markedly facilitate NMDA- and electrically evoked, but not AMPA-evoked responses in pyramidal cells of the rat medial prefrontal cortex (Arvanov and Wang 1998; Jardemark, Ai et al. 2001; Ninan and Wang 2003). This might account for the ability of atypical antipsychotics to reduce schizophrenic negative symptoms and in improving neuropsychological and cognitive functions (Hagger, Buckley et al. 1993; Beasley, Tollefson et al. 1997; Tollefson and Sanger 1997).

Since glycine and serine can bind to the modulatory site on NMDA receptors, they also can be used to investigate the relationship between antipsychotic action and NMDA receptor function. Chronic administration of a variety of antipsychotic drugs, both typical and atypical, affects glycine-stimulated NMDA receptor binding in several brain areas (McCoy and Richfield 1996). In the absence of glycine, haloperidol augmented NMDA receptor activity, but raising the extracellular glycine concentration reduced the effect of haloperidol, which therefore appears to be a partial agonist at the glycine binding site associated with the NMDAR complex (Lidsky, Yablonsky-Alter et al. 1997). Several studies reported results that were consistent with this interpretation (Waziri 1988; Rosse, Theut et al. 1989; Costa, Khaled et al. 1990; Fletcher and MacDonald 1993) (Javitt, Zylberman et al. 1994; Heresco-Levy, Javitt et al. 1996; Meador-Woodruff, King et al. 1996).

In a related approach, several groups have administered D-cycloserine, an antitubercular drug that acts as a relatively selective partial agonist at the glycine modulatory site (Watson, Bolanowski et al. 1990). D-cycloserine significantly improved negative symptoms when added to conventional antipsychotics, but it did not improve performance on a cognitive battery. D-cycloserine added to clozapine resulted in worsening of negative symptoms (Goff, Tsai et al. 1996; Goff, Tsai et al. 1999; Goff and Coyle 2001).

Several investigators have found that chronic antipsychotic treatment alters the expression of mRNA encoding glutamate receptor subunits, which varies depending on the drug type, the subunit, and the brain region (Meshul and Tan 1994; Meador-Woodruff, King et al. 1996; Healy and Meador-Woodruff 1997; Riva, Tascedda et al. 1997). In general, conventional antipsychotics increased the amount of mRNA encoding NMDA receptor subunits (NR1 and NR2 proteins) in the striatum, whereas clozapine treatment produced no change (Riva, Tascedda et al. 1997). This difference may be involved in the differential liability for extrapyramidal side effects during typical versus atypical AP treatment.

An important problem facing clinicians in the treatment of schizophrenia is the significant variability in clinical response to antipsychotic medications. At least one third of patients treated with traditional APs do not respond well, and only 30-60% of individuals resistant to typical antipsychotics may demonstrate a beneficial clinical response to clozapine with respect to positive and negative symptomatology (Basile, Masellis et al. 2002).

There is strong evidence to suggest that genetic variation plays an important role in inter-individual differences in medication response and toxicity. Molecular genetic approaches provide a novel method of dissecting the heterogeneity of psychotropic drug response. These pharmacogenetic strategies offer the prospect of identifying biological predictors of psychotropic drug response and could provide the means of determining the molecular substrates of drug efficacy and drug-induced adverse events. (Malhotra, Murphy & Kennedy, 2004).

Several studies have been conducted investigating the role of various receptor gene polymorphisms in association with response to clozapine. A few experiments have been conducted on the NR2B subunit gene (GRIN2B) polymorphisms in association with clozapine response: Hong et al (Hong, Yu et al. 2001) found positive association between the C2664T polymorphism and higher clozapine dosage in 100 Chinese treatment refractory patients. These results were replicated by Chiu et al (Chiu, Wang et al. 2003).

There is a need in the art to identify tests or assays that are predictive of a subject's response to drug therapy. Further, there is a need in the art for methods of identifying DNA polymorphisms that may be used to predict a patient's response to drug therapy. In addition, there is a need in the art to identify specific polymorphisms in DNA sequences that are predictive of negative symptom change during clozapine treatment.

SUMMARY OF THE INVENTION

The present invention relates to DNA polymorphisms. More specifically, the present invention relates to DNA polymorphisms that are predictive of a subject's response to drug treatment.

According to the present invention, there is provided a method (A) of identifying a subject having a propensity to respond to drug therapy comprising, a) isolating genomic DNA from a sample of the subject;
b) genotyping a T5988C marker of a GRIN2B gene wherein, the GRIN2B 5988 T/T genotype is predictive of a subject responsive to drug therapy.

Also according to the present invention, there is provided a method as defined above (method A) wherein the subject is a schizophenic subject.

The present invention further contemplates a method as defined above (method A) wherein the sample is a blood sample, a sample of saliva, cheek swab sample, a tissue sample, or a sample of a bodily fluid.

Also provided by the present invention is a method as defined above (method A), wherein genotyping the T5988C marker is performed by PCR analysis, sequence analysis, LCR analysis.

The present invention also provides the method as defined above (method A), wherein the drug therapy is clozapine therapy. Furthermore, the subject responsive to clozapine therapy exhibits a significant improvement of negative symptoms as measured using a psychiatric test. Examples of negative symptoms comprise restriction in the range and intensity of emotional expression, affective flattening, anhedonia, social withdrawl, restriction in the fluency and productivity of thought and speech, alogia, restriction in the initiation of goal-directed behaviour, avolition, lack of interest in activities, or a combination thereof.

The present invention also provides for a method (B) of predicting a negative symptom change in a subject during drug therapy comprising, a) isolating genomic DNA from a sample of the subject;
b) genotyping a T5988C marker of a GRIN2B gene wherein, the GRIN2B 5988 T/T genotype is predictive of a negative symptom improvement in the subject in response to drug therapy.

Also provided by the present invention is a method (C) of identifying a polymorphism in a nucleotide sequence of interest that is predictive of response to drug therapy comprising, a) assessing negative symptom improvement in a plurality of subjects during the course of drug therapy;
b) isolating a sample comprising DNA from each subject;
c) genotyping one or more nucleotide sequences of interest in the DNA of each subject to identify one or more polymorphisms that exist in the one or more nucleotide sequences of interest, wherein correlation of a significant improvement of negative symptoms with one or more polymorphisms is predictive of response to drug therapy.

Also contemplated by the present invention is a method as defined above wherein the sample is a blood sample, a sample of saliva, a cheek swab sample, a tissue sample, or a sample of bodily fluids.

Also contemplated by the present invention is a method as defined above wherein the drug therapy is antipsychotic drug therapy. In a further embodiment, the antipsychotic drug therapy may comprise colzapine therapy The present invention also provides a method as defined above wherein the sample comprising DNA is genomic DNA.

The present invention also contemplates a method as defined above wherein the genotyping is performed by PCR, LCR, or sequencing.

Also provided by the present invention is a method as defined above wherein the assessing negative symptom improvement is measured using a psychiatric test. Examples of negative symptoms comprise restriction in the range and intensity of emotional expression, affective flattening, anhedonia, social withdrawl, restriction in the fluency and productivity of thought and speech, alogia, restriction in the initiation of goal-directed behaviour, avolition, lack of interest in activities, or a combination thereof.

The method of the present invention further contemplates a method (D) of identifying a polymorphism in a nucleotide sequence of interest that is predictive of negative symptom change in schizophrenic subjects during antipsychotic drug therapy comprising, a) assessing negative symptom improvement in a plurality of schizophrenic subjects during the course of antipsychotic drug therapy;
b) isolating a sample comprising genomic DNA from the blood of each subject;
c) genotyping one or more nucleotide sequences of interest in the genomic DNA of each subject to identify one or more polymorphisms that exist in said one or more nucleotide sequences of interest, wherein correlation of a significant improvement of negative symptoms with one or more polymorphisms in a nucleotide sequence of interest is predictive of said polymorphism being associated with a positive response to antipsychotic drug therapy. The method as defined above may further comprise a separate step of correlating the one or more polymorphisms that exist with the subjects exhibiting a significant improvement in one or more negative symptoms.

This summary of the invention does not necessarily describe all necessary features of the invention but that the invention may also reside in a sub-combination of the described features.

DESCRIPTION OF PREFERRED EMBODIMENT

The present invention relates to DNA polymorphisms. More specifically, the present invention relates to DNA polymorphisms that are predictive of a subject's response to drug treatment.

The following description is of a preferred embodiment by way of example only.

According to the present invention, there is provided a method of identifying a subject having a propensity to respond to drug therapy comprising, a) isolating genomic DNA from a sample of the subject, and;

b) genotyping the T5988C marker in the 3'UTR of the GRIN2B gene wherein, the GRIN2B 5988 T/T genotype is predictive of the subject responsive to drug therapy.

According to a specific embodiment, the present invention, there is provided a method of identifying a subject having a propensity to respond to clozapine therapy comprising, a) isolating genomic DNA from a sample of the subject, and;

b) genotyping the T5988C marker in the 3'UTR of the GRIN2B gene wherein, the GRIN2B 5988 T/T genotype is predictive of a subject responsive to clozapine therapy.

In a preferred embodiment, which is not meant to be limiting in any manner, the subject is a schizophenic subject.

The present invention also provides for a method of predicting a negative symptom change in a subject during drug therapy comprising, a) isolating genomic DNA from a sample of the subject;

b) genotyping the T5988C marker in the 3'UTR of the GRIN2B gene wherein, the GRIN2B 5988 T/T genotype is predictive of a negative symptom improvement in the subject in response to drug therapy.

The sample obtained from a subject may comprise any biological sample from which genomic DNA may be isolated, for example, but not to be limited to a tissue sample, a sample of saliva, a cheek swab sample, blood, or other biological fluids that contain genomic DNA. In a preferred embodiment, which is not meant to be limiting in any manner, the sample is a blood sample.

Genotyping of the T5988C marker may be performed by any method known in the art, for example PCR, sequencing, ligation chain reaction (LCR) or any other standard method known in the art that may be used to determine SNPs (single nucleic acid polymorphisms). In a preferred embodiment, which is not meant to be limiting in any manner, genotyping of the T5988C marker is performed by PCR analysis using appropriate primers, probes and PCR conditions. Representative examples of primers, probes and PCR conditions that may be used are provided in the Examples.

By "negative symptom change" it is meant a change in a subject of a negative symptom (Criteron A5), for example but not limited to restriction in the range and intensity of emotional expression (affective flattening; anhedonia), social withdrawl, restriction in the fluency and productivity of thought and speech (alogia), and restriction in the initiation of goal-directed behaviour (avolition), lack of interest in activities. The change in negative symptoms may be determined using any suitable means, for example a psychiatric test where an increase or decrease in the rating in the scale used in the test is indicative of a change. For example, a negative symptom improvement indicates a lessenening in the severity of negative symptoms as measured over time.

In a preferred embodiment, the subject responsive to a drug therapy, for example, clozapine therapy, exhibits a significant improvement of negative symptoms as measured using the Brief Psychiatric Rating Scale subscale for negative symptoms (BPRSneg), the Schedule for Affective Disorders and Schizophrenia subscale for negative symptoms (SADSneg), or a combination thereof. Other rating scales may be used provided the improvement in negative symptoms can be appropriately measured.

In an alternate embodiment of the present invention, which is not meant to be limiting in any manner, there is provided a method of identifying a polymorphism in a nucleotide sequence of interest that is predictive of response to drug therapy comprising, a) assessing negative symptom improvement in a plurality of subjects during the course of drug therapy;

b) isolating a sample comprising DNA from each subject;

c) genotyping one or more nucleotide sequences of interest in the DNA of each subject to identify one or more polymorphisms that exist in the one or more nucleotide sequences of interest, wherein correlation of a significant improvement of negative symptoms with one or more polymorphisms is predictive of response to drug therapy.

In a preferred embodiment, but not wishing to be limiting in any manner, the sample as defined above may comprise a blood sample, a tissue sample, a sample of saliva, a cheek swab sample, a sample of bodily fluids, or any other appropriate sample from a subject containing DNA.

It is also contemplated that the drug therapy defined above may be antipsychotic drug therapy. Preferably, the drug interacts with the NMDA receptor subunit encoded by the GRIN2B gene. In a preferred embodiment, which is not meant to be limiting in any manner, the drug therapy comprises colzapine therapy. However, it is contemplated that other antipsychotic drugs may be employed in the method of the present invention.

The present invention also contemplates a method of identifying a polymorphism in a nucleotide sequence of interest that is predictive of negative symptom change in schizophrenic subjects during antipsychotic drug therapy comprising, a) assessing negative symptom improvement in a plurality of schizophrenic subjects during the course of antipsychotic drug therapy;

b) isolating a sample comprising genomic DNA from the blood of each subject;

c) genotyping one or more nucleotide sequences of interest in the genomic DNA of each subject to identify one or more polymorphisms that exist to identify one or more polymorphisms that exist in said one or more nucleotide sequences of interest, wherein correlation of a significant improvement of negative symptoms with one or more polymorphisms in a nucleotide sequence of interest is predictive of said polymorphism being associated with a positive response to antipsychotic drug therapy.

In a further embodiment, the method of the present invention also may comprise the step of correlating the one or more polymorphisms that exist with the subjects exhibiting a significant improvement in one or more negative symptoms.

As with all drugs, there is variability among individuals in clinical responses to antipsychotics. Pharmacogenetics can provide a novel foundation for understanding this interindividual variability in antipsychotic response, and may provide an avenue for predicting patient propensity to respond and to develop antipsychotic side effects a priori (Basile, Masellis et al. 2002).

The role of the GRIN2B gene 3'UTR region in negative symptom improvement was examined in response to six months of clozapine treatment. Allelic variation the GRIN2B gene was found to significantly predict negative symptoms improvement for patients with the GRIN2B 5988 T/F genotype.

Previous studies have shown positive association between another GRIN2B marker, the C2664T polymorphism and response to overall clozapine treatment (Hong, Yu et al. 2001). Our results are different than these findings since we focus on the clinically important domain of negative symptoms. Due to the size of the current study the method disclosed has prospective clinical assessments of response.

The precise mechanism of clozapine action might involve many different receptors and, thus may be genetically heterogeneous. Similarly, the interaction of other drugs with the NMDA receptor subunit encoded by the GRIN2B gene may be effected by the T5988C polymorphism. The T5988C polymorphism does not induce changes in the amino acid sequence. Functional effects on mRNA stability or other gene expression mechanisms are as yet unknown for this marker. GRIN2B is most probably one among numerous genes that are involved in the modulation of clozapine response, however, by itself it provides meaningful prediction of negative symptom response. The strengths of k our sample include: 1) it was a prospective clinical trial, not a cross-sectional or historical assessment 2) relatively detailed clinical data were collected, 3) patients were monitored for compliance via testing of medication blood levels during the treatment duration, and 4) there were repeated clinical assessments during the six months of treatment.

The above description is not intended to limit the claimed invention in any manner.

The present invention will be further illustrated in the following examples. However it is to be understood that these examples are for illustrative purposes only, and should not be used to limit the scope of the present invention in any manner.

EXAMPLE 1

Our sample consisted of 90 schizophrenic subjects treated with clozapine. The majority of the patients were Caucasian. The second most represented ethnicity was African American. The ratio of males to females was approximately 2.5:1. The overall response to clozapine treatment over six months was assessed using the Brief Psychiatric Rating Scale (BPRS) and the Schedule for Affective Disorders and Schizophrenia (SADS). The sample is composed of a group of patients from the Cleveland area (obtained from Dr. H. Y Meltzer, Case Western Reserve University), as part of a multisite coordinated clinical trial of clozapine response. Data on the specific assessment of negative symptom improvement in response to clozapine treatment were collected over a six month period (baseline minus 6 month score). Negative symptom improvement over a period of six months was assessed using the Brief Psychiatric Rating Scale subscale for negative symptoms (BPRSneg), and the Schedule for Affective Disorders and Schizophrenia subscale for negative symptoms (SADSneg).

Three 10 cc EDTA tubes of blood were drawn from patients. The EDTA tubes were used for direct extraction of genomic DNA using the high salt extraction method of Lahiri et al, 1991.

GRIN2B Markers:

The T5988C marker is located in the 3'UTR. The T5072G, the A5806C marker and the T5988C are in partial linkage disequilibrium. All polymorphisms were in Hardy-Weinberg equilibrium in our sample.

Under the following conditions: DNA 2.5 ml; 10×PCR Buffer 2.5 ml; 2 mM $MgCl_2$ 1.5 ml; 2% gelatine 0.125 ml; primers (10 pmol/ml) 1 ml; dNTP 0.5 ml; Taq polymerase (5 U/ml) 0.2 ml; $H_2O$ (to 25 ml) 15.175 ml. The PCR program consisted of an initial denaturation at 95° for 5', followed by 35 cycles at 95° for 20", 60° for 20", 72° for 20", and a final extension at 72° for 4'. Digestion was performed with restriction enzyme BSTYI; amplified products were digested overnight at 60° C. and then resolved on 3% agarose gel.

The T5988C marker was genotyped using primers, probes and PCR conditions developed by Applied Biosystems Inc.

The primer pair sequences for the T5988C marker were:

```
CTTGAGCCCAGAGTGAACACT          (SEQ ID NO: 1)

ACCCTCATCCCTGGAGTTTTATACA      (SEQ ID NO: 2)
```

Amplification and detection of the PCR products were performed with an ABI Prism 7000 sequence detection instrument (Applied Biosystems Inc.), as suggested by the manufacturer, by use of all default program settings. The PCR protocol was as follows: DNA 50 ng; TaqMan MasterMix 5 ml; Assay 0.25 ml; $dH_2O$ 3.75 ml. Cycling conditions were as follows: after 10 min at 95° C., the samples were submitted to 40 cycles, each consisting of a step at 95° C. for 15 s, followed by a step at 60° C. for 1 min. The PCR product was detected as an increase in fluorescence during the PCR extension phase when the probe was cleaved by the 5' exonuclease activity of the Taq DNA polymerase. This cleavage interrupts the fluorescence resonance energy transfer and the reporter dye fluoresces in proportion to the level of PCR product generated.

Statistical Analysis

Analysis of Covariance (ANCOVA) was performed in order to test the effect of genotype on negative symptom improvement as measured by the SADSneg subscale. The baseline score for the SADSneg, assessed before the clozapine treatment was started, was used as a covariate, in part to control for regression to the mean effects.

Results

The T5988C marker was associated with significant improvement of negative symptoms measured with SADSneg (see table 1).

TABLE 1

Negative symptom response ANCOVA for SADSneg.

| | SADSneg mean | | | | |
|---|---|---|---|---|---|
| | C C | C T | T T | | SADSneg |
| GRIN2B C5988T | 1.3 | 1.26 | 1.87 | F = 3.67 | p = 0.03 |

SADSneg baseline scores were used as a covariate. The 'SADSneg mean' is the mean converted change score (baseline minus 6 month score) of the SADSneg subscale after six months of clozapine treatment.

All citations are herein incorporated by reference.

The present invention has been described with regard to preferred embodiments. However, it will be obvious to persons skilled in the art that a number of variations and modifications can be made without departing from the scope of the invention as described herein.

CITATIONS/REFERENCES

Angrist, B., E. Peselow, et al. (1982). "Partial improvement in negative schizophrenic symptoms after amphetamine." *Psychopharmacology (Berl)* 78(2): 128-30.

Arvanov, V. L. and R. Y. Wang (1998). "M100907, a selective 5-HT2A receptor antagonist and a potential antipsychotic drug, facilitates N-methyl-D-aspartate-receptor mediated neurotransmission in the rat medial prefrontal cortical neurons in vitro." *Neuropsychopharmacology* 18(3): 197-209.

Arvanov, V. L., X. Liang, et al. (1997). "Clozapine and haloperidol modulate N-methyl-D-aspartate- and non-N-methyl-D-aspartate receptor-mediated neurotransmission in rat prefrontal cortical neurons in vitro." *J Pharmacol Exp Ther* 283(1): 226-34.

Basile, V. S., M. Masellis, et al. (2002). "Pharmacogenomics in schizophrenia: the quest for individualized therapy." *Hum Mol Genet* 11(20): 2517-30.

Beasley, C. M., Jr., G. D. Tollefson, et al. (1997). "Efficacy of olanzapine: an overview of pivotal clinical trials." *J Clin Psychiatry* 58 Suppl 10: 7-12.

Bhana, N., R. H. Foster, et al. (2001). "Olanzapine: an updated review of its use in the management of schizophrenia." *Drugs* 61(1): 111-61.

Carlsson, M. and A. Carlsson (1990). "Schizophrenia: a subcortical neurotransmitter imbalance syndrome?" *Schizophr Bull* 16(3): 425-32.

Chen, L. and C. R. Yang (2002). "Interaction of dopamine D1 and NMDA receptors mediates acute clozapine potentiation of glutamate EPSPs in rat prefrontal cortex." *J Neurophysiol* 87(5): 2324-36.

Chiu, H. J., Y. C. Wang, et al. (2003). "Association analysis of the genetic variants of the N-methyl D-aspartate receptor subunit 2b (NR2b) and treatment-refractory schizophrenia in the Chinese." *Neuropsychobiology* 47(4): 178-81.

Corbett, R., F. Camacho, et al. (1995). "Antipsychotic agents antagonize non-competitive N-methyl-D-aspartate antagonist-induced behaviors." *Psychopharmacology (Berl)* 120(1): 67-74

Costa, J., E. Khaled, et al. (1990). "An open trial of glycine as an adjunct to neuroleptics in chronic treatment-refractory schizophrenics." *J Clin Psychopharmacol* 10(1): 71-2.

Daly, D. A. and B. Moghaddam (1993). "Actions of clozapine and haloperidol on the extracellular levels of excitatory amino acids in the prefrontal cortex and striatum of conscious rats." *Neurosci Lett* 152(1-2): 61-4.

Davis, K. L., R. S. Kahn, et al. (1991). "Dopamine in schizophrenia: a review and reconceptualization." *Am J Psychiatry* 148(11): 1474-86.

Farber, N. B., J. Foster, et al. (1996). "Olanzapine and fluperlapine mimic clozapine in preventing MK-801 neurotoxicity." *Schizophr Res* 21(1): 33-7

Farber, N. B., M. T. Price, et al. (1993). "Antipsychotic drugs block phencyclidine receptor-mediated neurotoxicity." *Biol Psychiatry* 34(1-2): 119-21

Fletcher, E. J. and J. F. MacDonald (1993). "Haloperidol interacts with the strychnine-insensitive glycine site at the NMDA receptor in cultured mouse hippocampal neurones." *Eur J Pharmacol* 235(2-3): 291

Goff, D. C. and J. T. Coyle (2001). "The emerging role of glutamate in the pathophysiology and treatment of schizophrenia." *Am J Psychiatry* 158(9): 1367-77

Goff, D. C., G. Tsai, et al. (1996). "D-cycloserine added to clozapine for patients with schizophrenia." *Am J Psychiatry* 153(12): 1628-30.

Goff, D. C., G. Tsai, et al. (1999). "A placebo-controlled trial of D-cycloserine added to conventional neuroleptics in patients with schizophrenia." *Arch Gen Psychiatry* 56(1): 21-7.

Hagger, C., P. Buckley, et al. (1993). "Improvement in cognitive functions and psychiatric symptoms in treatment-refractory schizophrenic patients receiving clozapine." *Biol Psychiatry* 34(10): 702-12.

Healy, D. J. and J. H. Meador-Woodruff (1997). "Clozapine and haloperidol differentially affect AMPA and kainate receptor subunit mRNA levels in rat cortex and striatum." *Brain Res Mol Brain Res* 47(1-2): 331-8.

Heresco-Levy, U., D. C. Javitt, et al. (1996). "Double-blind, placebo-controlled, crossover trial of glycine adjuvant therapy for treatment-resistant schizophrenia." *Br J Psychiatry* 169(5): 610-7

Hong, C. J., Y. W. Yu, et al. (2001). "Association analysis for NMDA receptor subunit 2B (GRIN2B) genetic variants and psychopathology and clozapine response in schizophrenia." *Psychiatr Genet* 11(4): 219-22.

Jardemark, K. E., J. Ai, et al. (2001). "Biphasic modulation of NMDA-induced responses in pyramidal cells of the medial prefrontal cortex by Y-931, a potential atypical antipsychotic drug." *Synapse* 41(4): 294-300

Javitt, D. C. (2001). "Management of negative symptoms of schizophrenia." *Curr Psychiatry Rep* 3(5): 413-7.

Javitt, D. C., I. Zylberman, et al. (1994). "Amelioration of negative symptoms in schizophrenia by glycine." *Am J Psychiatry* 151(8): 1234-6

Lidsky, T. I., E. Yablonsky-Alter, et al. (1993). "Antiglutamatergic effects of clozapine." *Neurosci Lett* 163(2): 155-8.

Lidsky, T. I., E. Yablonsky-Alter, et al. (1997). "Antipsychotic drug effects on glutamatergic activity." *Brain Res* 764(1-2): 46-52.

Malhotra, A. K., G. M. Murphy, Jr., et al. (2004). "Pharmacogenetics of psychotropic drug response." *Am J Psychiatry* 161(5): 780-96.

McCoy, L. and E. K. Richfield (1996). "Chronic antipsychotic treatment alters glycine-stimulated NMDA receptor binding in rat brain." *Neurosci Lett* 213(2): 137-41.

Meador-Woodruff, J. H. and D. J. Healy (2000). "Glutamate receptor expression in schizophrenic brain." *Brain Res Brain Res Rev* 31(2-3): 288-94.

Meador-Woodruff, J. H., R. E. King, et al. (1996). "Differential regulation of hippocampal AMPA and kainate receptor subunit expression by haloperidol and clozapine." *Mol Psychiatry* 1(1): 41-53.

Meshul, C. K. and S. E. Tan (1994). "Haloperidol-induced morphological alterations are associated with changes in calcium/calmodulin kinase II activity and glutamate immunoreactivity." *Synapse* 18(3): 205-17

Ninan, I. and R. Y. Wang (2003). "Modulation of the ability of clozapine to facilitate NMDA- and electrically evoked responses in pyramidal cells of the rat medial prefrontal cortex by dopamine: pharmacological evidence." *Eur J Neurosci* 17(6): 1306-12.

Nomikos, G. G., M. Iurlo, et al. (1994). "Systemic administration of amperozide, a new atypical antipsychotic drug, preferentially increases dopamine release in the rat medial prefrontal cortex." *Psychopharmacology (Berl)* 115(1-2): 147-56.

Olney, J. W. and N. B. Farber (1994). "Efficacy of clozapine compared with other antipsychotics in preventing NMDA-antagonist neurotoxicity." *J Clin Psychiatry* 55 Suppl B: 43-6.

Olney, J. W. and N. B. Farber (1995). "Glutamate receptor dysfunction and schizophrenia." *Arch Gen Psychiatry* 52(12): 998-1007.

Riva, M. A., F. Tascedda, et al. (1997). "Regulation of NMDA receptor subunit messenger RNA levels in the rat brain following acute and chronic exposure to antipsychotic drugs." *Brain Res Mol Brain Res* 50(1-2): 136-42.

Rosse, R. B., S. K. Theut, et al. (1989). "Glycine adjuvant therapy to conventional neuroleptic treatment in schizophrenia: an open-label, pilot study." *Clin Neuropharmacol* 12(5): 416-24.

Tollefson, G. D. and T. M. Sanger (1997). "Negative symptoms: a path analytic approach to a double-blind, placebo- and haloperidol-controlled clinical trial with olanzapine." *Am J Psychiatry* 154(4): 466-74.

van Kammen, D. P. and J. J. Boronow (1988). "Dextro-amphetamine diminishes negative symptoms in schizophrenia." *Int Clin Psychopharmacol* 3(2): 111-21.

Wang, J. and P. O'Donnell (2001). "D(1) dopamine receptors potentiate nmda-mediated excitability increase in layer V prefrontal cortical pyramidal neurons." *Cereb Cortex* 11(5): 452-62.

Wang, R. Y. and X. Liang (1998). "M100907 and clozapine, but not haloperidol or raclopride, prevent phencyclidine-induced blockade of NMDA responses in pyramidal neurons of the rat medial prefrontal cortical slice." *Neuropsychopharmacology* 19(1): 74-85.

Watanabe, M. and Y. Hagino (1999). "The atypical antipsychotic sertindole enhances efflux of dopamine and its metabolites in the rat cortex and striatum." *Eur J Pharmacol* 367(1): 19-23.

Watson, G. B., M. A. Bolanowski, et al. (1990). "D-cycloserine acts as a partial agonist at the glycine modulatory site of the NMDA receptor expressed in Xenopus oocytes." *Brain Res* 510(1): 158-6

Waziri, R. (1988). "Glycine therapy of schizophrenia." *Biol Psychiatry* 23(2): 210-1.

Weinberger, D. R., K. F. Berman, et al. (1986). "Physiologic dysfunction of dorsolateral prefrontal cortex in schizophrenia. I. Regional cerebral blood flow evidence." *Arch Gen Psychiatry* 43(2): 114-24.

Weinberger, D. R., K. F. Berman, et al. (1988). "Physiological dysfunction of dorsolateral prefrontal cortex in schizophrenia. III. A new cohort and evidence for a monoaminergic mechanism." *Arch Gen Psychiatry* 45(7): 609-15.

Westerink, B. H., P. de Boer, et al. (1998). "Antipsychotic drugs induce similar effects on the release of dopamine and noradrenaline in the medial prefrontal cortex of the rat brain." *Eur J Pharmacol* 361(1): 27-33.

Yamamoto, B. K., E. A. Pehek, et al. (1994). "Brain region effects of clozapine on amino acid and monoamine transmission." *J Clin Psychiatry* 55 Suppl B: 8-14.

The embodiments of the invention in which an exclusive property of privilege is claimed are defined as follows:

1. A method of identifying a human schizophrenic subject having a propensity to respond to clozapine drug therapy, comprising:

a) isolating genomic DNA from a sample of the subject;

b) genotyping a T5988C marker of a GRIN2B gene; and c) identifying the propensity said human schizophrenic subject to respond to clozapine drug therapy based on said genotyping of the T5988C marker of the GRIN2B gene;

wherein a GRIN2B 5988 T/T genotype identifies the human schizophrenic subject as having a higher propensity to respond to clozapine drug therapy, relative to a GRIN2B 5988 C/C genotype or a GRIN2B 5988 C/T genotype, and wherein responding to clozapine drug therapy comprises an improvement in negative symptoms selected from the group consisting of the range and intensity of emotional expression, affective flattening, anhedonia, social withdrawal, restriction in the fluency and productivity of thought and speech, alogia, restriction in the initiation of goal-directed behavior, avolition, lack of interest in activities, or a combination thereof.

2. The method of claim 1, wherein the sample is a blood sample, saliva, cheek swab, a tissue sample, or a sample of a bodily fluid.

3. The method of claim 1, wherein genotyping the T5988C marker is performed by PCR analysis.

4. The method of claim 1, wherein a subject having the GRIN2B 5988T/T genotype exhibits a significant improvement of negative symptoms as measured using a psychiatric test.

5. The method of claim 1, wherein the human schizophrenic subject is a male human schizophrenic subject.

6. The method of claim 5, wherein the sample is a blood sample, saliva, cheek swab, a tissue sample, or a sample of a bodily fluid.

7. The method of claim 5, wherein genotyping the T5988C marker is performed by PCR analysis.

8. The method of claim 5, wherein a subject having the GRIN2B 5988T/T genotype exhibits a significant improvement of negative symptoms as measured using a psychiatric test.

9. The method of claim 1, wherein the human schizophrenic subject is a female human schizophrenic subject.

10. The method of claim 9, wherein the sample is a blood sample, saliva, cheek swab, a tissue sample, or a sample of a bodily fluid.

11. The method of claim 9, wherein genotyping the T5988C marker is performed by PCR analysis.

12. The method of claim 9, wherein a subject having the GRIN2B 5988T/T genotype exhibits a significant improvement of negative symptoms as measured using a psychiatric test.

* * * * *